(12) United States Patent
McMichael et al.

(10) Patent No.: US 6,896,141 B2
(45) Date of Patent: May 24, 2005

(54) SURGICAL KIT WITH MULTIPLE PLANAR RECESS SURFACES

(75) Inventors: Donald J. McMichael, South Jordan, UT (US); Mark E. Foster, Sandy, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/085,639

(22) Filed: Feb. 28, 2002

(65) Prior Publication Data

US 2003/0159969 A1 Aug. 28, 2003

(51) Int. Cl.[7] .............................................. B65D 85/00
(52) U.S. Cl. ....................... 206/571; 206/370; 206/562; 206/570; 220/527
(58) Field of Search ......................... 206/564, 363–370, 206/438, 439, 440, 570–572; 220/527, 528

(56) References Cited

U.S. PATENT DOCUMENTS

| | | | |
|---|---|---|---|
| 4,085,845 A | * | 4/1978 | Perfect ....................... 206/564 |
| 4,170,300 A | | 10/1979 | Pick |
| 4,293,074 A | * | 10/1981 | Dunsky ...................... 206/572 |
| D277,508 S | | 2/1985 | Clair |
| 4,522,302 A | | 6/1985 | Paikoff |
| 4,523,679 A | | 6/1985 | Paikoff et al. |
| D281,704 S | | 12/1985 | Deacon |
| D282,279 S | | 1/1986 | Holewinski et al. |
| D282,280 S | | 1/1986 | Holewinski et al. |
| 4,573,576 A | | 3/1986 | Krol |
| 4,595,102 A | * | 6/1986 | Cianci et al. ............... 206/572 |
| D288,481 S | | 2/1987 | Holewinski et al. |
| D288,606 S | | 3/1987 | Blatherwick et al. |
| 4,739,883 A | | 4/1988 | Mohs et al. |
| 4,828,113 A | | 5/1989 | Friedland et al. |
| 4,886,165 A | | 12/1989 | Annett |
| 4,928,830 A | | 5/1990 | Brewer |
| 5,011,020 A | | 4/1991 | Stevens et al. |
| 5,031,768 A | | 7/1991 | Fischer |
| 5,031,775 A | | 7/1991 | Kane |
| 5,058,580 A | | 10/1991 | Hazard |
| 5,098,391 A | * | 3/1992 | Pantages et al. ............ 604/159 |
| 5,112,310 A | | 5/1992 | Grobe |
| 5,117,981 A | | 6/1992 | Crawford et al. |
| 5,144,942 A | | 9/1992 | Decarie et al. |
| 5,178,282 A | | 1/1993 | Williams |
| D341,159 S | | 11/1993 | Watson et al. |
| 5,289,919 A | * | 3/1994 | Fischer ....................... 206/571 |
| 5,311,990 A | | 5/1994 | Kalinski |
| 5,315,985 A | | 5/1994 | Decarie et al. |
| 5,318,543 A | | 6/1994 | Ross et al. |

(Continued)

FOREIGN PATENT DOCUMENTS

| | | |
|---|---|---|
| EP | 0407663 B1 | 1/1991 |
| WO | 9508302 | 3/1995 |
| WO | 9607364 | 4/1996 |
| WO | 0057810 | 10/2000 |

OTHER PUBLICATIONS

U.S. Appl. No. 10/085,637, filed Feb. 28, 2002.
U.S. Appl. No. 10/085,630, filed Feb. 28, 2002.
U.S. Appl. No. 10/085,417, filed Feb. 28, 2002.
Patent Abstract of Japan No. 10229964 Sep. 02, 1998.

*Primary Examiner*—Jim Foster
(74) *Attorney, Agent, or Firm*—Dority & Manning, P.A.

(57) ABSTRACT

A surgical kit, for example a percutaneous endoscopic gastrostomy kit, includes a tray having a plurality of recesses formed therein for receiving surgical implements. A substantially rigid accessory item container is received in a container recess defined in the tray. The container is removable from the tray and includes a base member and a lid. A securing device may be configured between the base member and the lid so that the container is reclosable.

20 Claims, 6 Drawing Sheets

U.S. PATENT DOCUMENTS

| | | | |
|---|---|---|---|
| 5,379,895 A | | 1/1995 | Foslien |
| 5,392,918 A | * | 2/1995 | Harrison .................... 206/571 |
| 5,449,071 A | * | 9/1995 | Levy .......................... 206/569 |
| 5,456,361 A | | 10/1995 | Walsh et al. |
| 5,507,279 A | | 4/1996 | Fortune et al. |
| D376,652 S | | 12/1996 | Hunt et al. |
| 5,590,778 A | | 1/1997 | Dutchik |
| 5,611,780 A | | 3/1997 | Decarie et al. |
| 5,699,909 A | | 12/1997 | Foster |
| 5,772,031 A | | 6/1998 | Landis |
| 5,779,053 A | | 7/1998 | Partika et al. |
| 5,848,700 A | | 12/1998 | Horn |
| 5,947,284 A | | 9/1999 | Foster |
| 5,947,296 A | | 9/1999 | Castora |
| 6,012,586 A | | 1/2000 | Misra |
| 6,036,021 A | | 3/2000 | Moi |
| 6,039,183 A | | 3/2000 | Rudnick et al. |
| 6,090,073 A | | 7/2000 | Gill |
| 6,093,179 A | | 7/2000 | O'Hara et al. |
| 6,112,900 A | | 9/2000 | Adkins, Jr. |
| 6,116,426 A | | 9/2000 | Slonim |
| D450,391 S | | 11/2001 | Hunt et al. |

* cited by examiner

SURGICAL KIT WITH MULTIPLE PLANAR RECESS SURFACES

BACKGROUND

The present invention relates to pre-packaged surgical kits in general, and more particularly to surgical kits for percutaneous endoscopic procedures.

Various medical procedures are simplified by providing the physician with a kit that contains the majority, if not all, of the necessary medical articles that the physician will need to complete a particular procedure. Kits may include articles such as, for example, drapes, syringes, scalpels, needles, clamps, gauze, sponges, drugs, sutures, and devices. Such kits are commonly provided for procedures such as, for example, percutaneous endoscopic gastrostomy ("PEG") and laparoscopic jejunostomy. These kits reduce the time spent by hospital personnel gathering the appropriate articles that are required for a particular procedure and ensure that the surgeon has each article at hand at the appropriate point in the procedure.

While many current surgical kits include the necessary medical implements or articles to complete a particular procedure, the articles in such kits may not be arranged in the most effective and efficient manner within the kits.

Also, conventional kits provide not only the surgical implements, such as scalpels, needles, scissors, and the like, but also "accessory" items such as swabs, gauze pads, single-use packages of ointments and lubricants, suture strands, sponges, and the like. These relatively small, loose, items are, however, relatively difficult to store in the kits. Such items may be simply placed loosely in the kit or provided in a sealed pouch. Once the kits or pouches are opened, these items tend to clutter the kit or are moved out of the kit to various locations by the surgical staff. It is difficult to maintain accountability of the items. Also, the accessory items are generally single-use disposable items and conventional kits do not provide a means for accountability and disposal of the devices after use.

SUMMARY

Objects and advantages of the invention will be set forth in part in the following description, or may be obvious from the description, or may be learned through practice of the invention.

The present invention provides a surgical kit of the type wherein the contents of the kit include surgical articles and accessory items to be used in performing a particular type of surgery. An example of such a kit is a percutaneous endoscopic gastrostomy (PEG) kit. It should be appreciated, however, that kits according to the present invention are not limited to any particular set of contents or any particular surgical procedure. The teachings of the present invention are beneficial for any pre-packaged surgical kit.

An embodiment of a surgical kit according to the invention includes a tray having a plurality of recesses formed therein for receiving surgical articles or implements useful in performing a particular surgical procedure. The terms surgical "articles" or "implements" are intended to encompass any combination of devices used in a surgical procedure and may include, without limitation, scissors, clamps, forceps, medicines and drugs, syringes, needles, tubes, scalpels, snares, cannulas, and so forth. Particular types of procedures require specific surgical articles, as is well understood by those skilled in the art. For example, a PEG kit may also include a "push" or "pull" assembly, a bolus adapter assembly, locking ring, snare device, etc.

The kit may also include any combination of "accessory" surgical items. The term "accessory" item is meant to encompass generally loose ancillary articles such as any number of pre-packaged single-use disposable items. Such items may include, for example, sutures, swabs, ointment packages, lubricant packages, drapes, gauze pads, small vials or packages of drugs, and the like. In this regard, the kit according to the invention may include an accessory item container received in a container recess defined in the tray. The accessory items may be placed in a separate container which is then placed in the tray prior to sealing the tray. The container may be seated in a respective recess defined in the tray.

The tray generally includes a cover that is sealed thereto, for example by an adhesive around a peripheral edge of the tray. In order to gain access to the contents of the tray, the cover is peeled or removed from the tray.

The tray includes a plurality of planar surfaces formed therein. The plurality of recesses are defined in the planar surfaces. The planar surfaces are offset vertically such that each planar surface is offset with respect to at least one other planar surface. In this manner, unobstructed access to certain of the recesses in at least one of the lower planar surfaces is obtained by removing articles from recesses in at least one upper planar surface. In particular embodiments, a first planar surface, a second planar surface and a third planar surface may be provided in the tray. The second planar surface may be offset from the first planar surface. The third planar surface may be offset from the first planar surface.

A particular embodiment of a surgical kit according to the invention is a PEG kit wherein each recess is adapted to hold an article that is useful in performing a percutaneous endoscopic gastrostomy. At least one of the recesses may be adapted to retain at least a portion of a percutaneous endoscopic gastrostomy tube. In some embodiments, such a recess may be disposed on the second planar surface. A retrieval snare and/or a guide wire may be positioned over at least a portion of the percutaneous endoscopic gastrostomy tube. One of the recesses may be adapted to retain a looped placement wire. In particular embodiments, such a recess may be disposed on the first surface. One of the recesses may be adapted to retain an exterior tube retention device, and such a recess may be disposed on the second planar surface in some embodiments. Another of the recesses may be adapted to retain an introducer cannula, and such a recess may be disposed in the third planar surface.

Some of the planar surfaces may have one or more bosses extending upwardly therefrom. In some embodiments, at least one boss may extend upwardly from the second planar surface. At least one boss may be disposed upon the first planar surface. An article may be positioned so that at least a portion of such an article is disposed about a boss.

The invention will be explained below in further detail by way of reference to an embodiment of the invention illustrated in the figures.

DETAILED DESCRIPTION

Reference will now be made in detail to embodiments of the invention, one or more examples of which are illustrated in the figures. The embodiments are provided by way of explanation of the invention, and not meant as a limitation of the invention. For example, features illustrated or described as part of one embodiment may be used with another embodiment to yield still a different embodiment. It is intended that the invention include these and other modifications as come within the scope and spirit of the invention.

An embodiment of a surgical kit is illustrated in the figures as a percutaneous endoscopic gastrostomy ("PEG") kit 20. It should be understood that a PEG kit is illustrated and described herein as merely representative of an embodiment of a surgical kit according to the invention, and that the invention is not limited to a PEG kit or any other particular type of kit. A PEG procedure is utilized to place a feeding tube into a patient that extends from the interior of the patient's stomach exteriorly of the patient. The feeding tube permits nutrients to be placed directly into a patient's stomach. This may be necessary when a patient has a disorder of the gastrointestinal tract, malabsorption (impaired absorption of nutrients, vitamins or minerals from the diet by the lining of the small intestine), or neurological or renal disorders. The feeding tube inserted using a PEG procedure is kept in place until a stoma is formed. Once a stoma is formed, a patient may remove and replace the PEG feeding tube with an alternate feeding device.

The PEG kit 20 may include a tray 22 having a plurality of planar surfaces and a plurality of recesses that may be disposed within the planar surfaces. The tray 22 may be formed of any suitable material, for example the tray 22 may be molded from a transparent or translucent substantially rigid plastic material (i.e., PETG). The tray 22 may have side walls 23 defining a depth of the tray 22.

As described in more detail below, the planar surfaces may be vertically offset within the tray 22. For example, referring to FIGS. 1, 5, and 6, a plurality of substantially horizontal planar surfaces 64, 66, 68, and 70 are defined in the tray 22. The planar surfaces may be co-molded with the tray 22. Each of the planar surfaces is vertically offset within the tray 22 with respect to at least one other planar surface.

A plurality of recesses adapted to hold articles or implements that are useful in performing the intended surgical procedure are defined in the various planar surfaces 64, 66, 68, and 70. Each recess may be adapted to hold one or more articles. Examples of recess configurations and respective articles held therein are discussed in greater detail below. The recesses may also include detents, protrusions, or the like to frictionally engage and retain the articles within the respective recesses.

Figure 1:
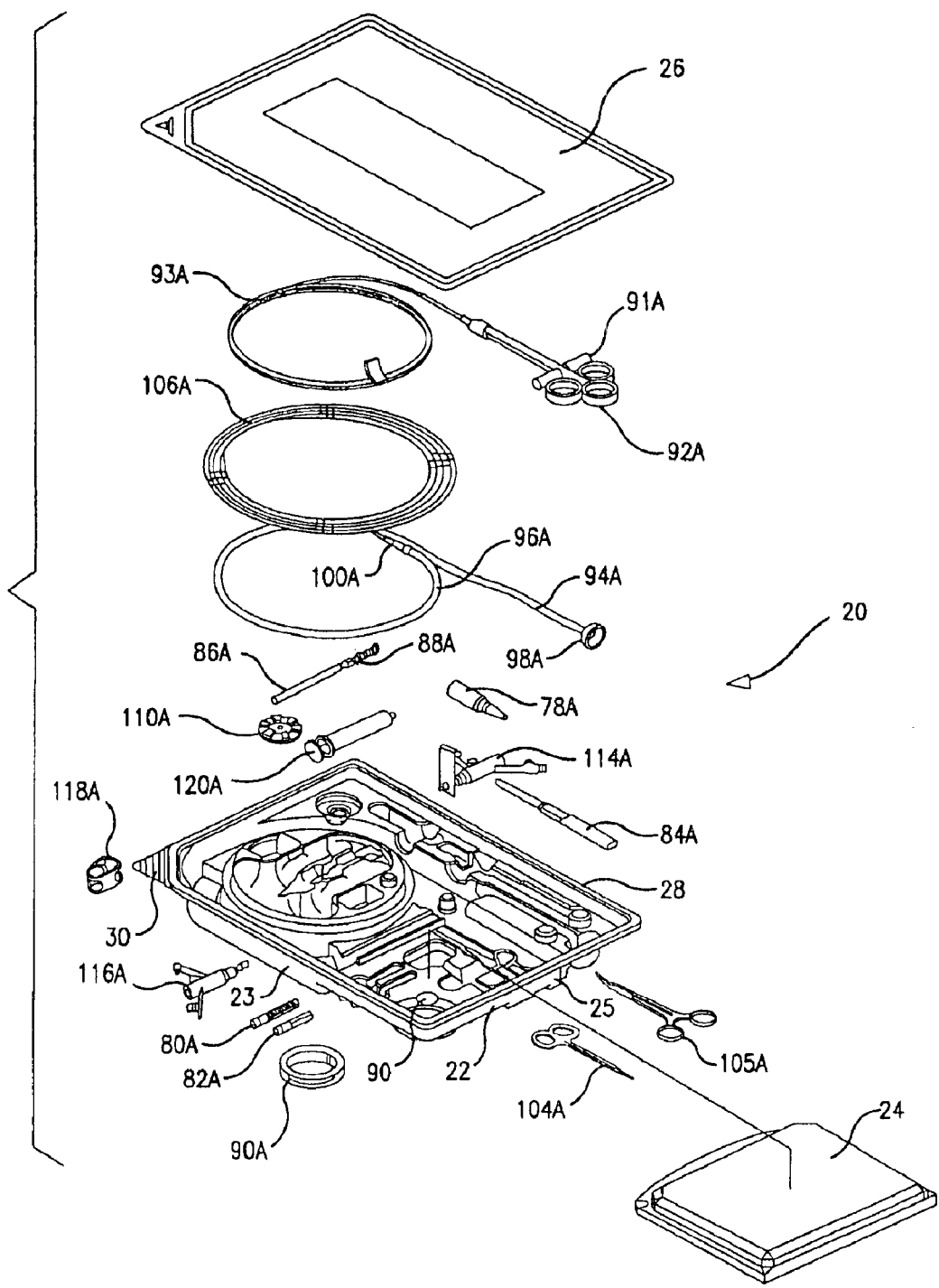
FIG. 1 is a perspective component view of an embodiment of a surgical kit according to the present invention.

As seen in FIG. 1, a cover 26 may be positioned on the tray 22 and, in some embodiments, may be adhered to a relatively flat peripheral surface 28 of the tray 22. A corner 30 of the tray 22 may be configured so that the cover 26 is not adhered to the corner 30. In such an embodiment, a user may grasp the cover 26 that is positioned adjacent to the corner 30 to remove the cover 26 from the tray 22. The cover may be attached to the tray by any suitable method, including but not limited to adhesives, heat sealing, sonic or thermal welding, solvents, etc. Once all of the articles have been placed into the tray 22 and the cover sealed to the tray, the kit is subjected to ETO gas sterilization.

A suitable cover material is Tyvek™, a spunbond polyolefin, from DuPont of Wilmington, Del. Any number of other permeable web materials suitable for ETO (ethylene oxide) gas sterilization, such as Kraft paper, may be used as the cover 26.

As illustrated generally in the figures, a container 24 is provided with the kit 20. The container is desirably a substantially rigid structure adapted to fit at least partially within the tray 22. For example, the container 24 may rest upon the planar surface 64. Desirably, the container 24 is disposed generally at the top of the tray so that access is provided to the container 24 immediately upon removing the cover 26 from the tray 22. In this way, the container 24 can be the first item removed from the tray 22 without touching or displacing any of the other articles in the tray 22. The tray side walls 23 and a bumper wall 126 define a recess or nesting place for the container and engage or retain the container 24 in a precise location within the tray 22. In one embodiment, the container 24 may be press-fitted into the nesting place. In another embodiment, the container 24 may be loosely received into the nesting place.

Figure 3:
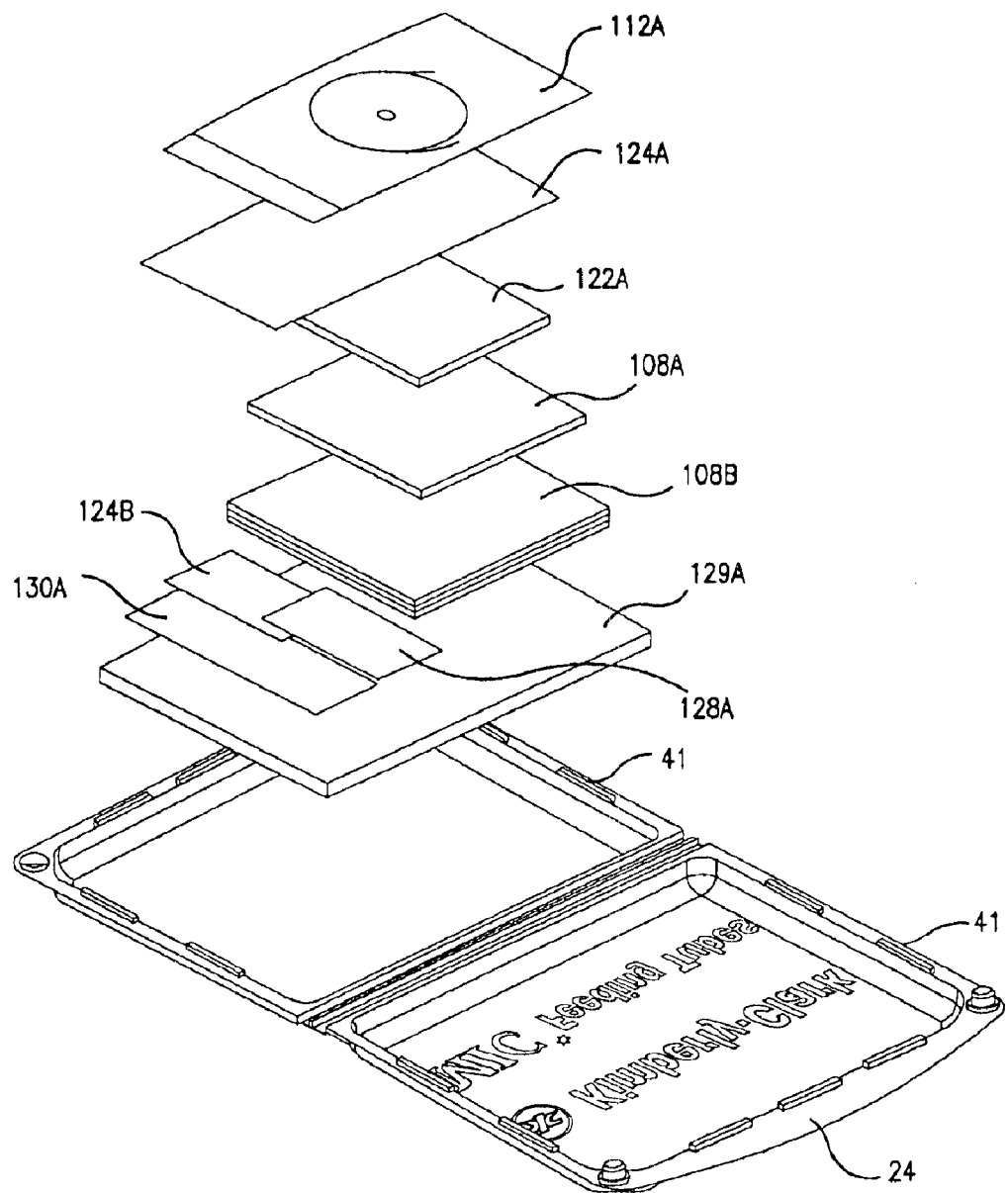
FIG. 3 is a perspective component view of an embodiment of the container according to the invention having been removed from the tray.

FIG. 3 illustrates an embodiment of a container 24 that may be used in the present invention. The container 24 may include a substantially rigid lid 34 and a base 36, the lid 24 and the base 36 being flexibly attached to each other by a hinge 38 (i.e., a living hinge). In some embodiments, the lid 34 and the base 36 may not be attached to each other, or may be attached to each other using alternate configurations. The container may be molded or otherwise formed from the same polymer material as the tray 22. A lip 40 may be provided that extends around the edges of the lid 34 and the base 36. In particular embodiments, an extended portion 42 may be disposed along one edge of the lip 40 to enable a user to more easily open the container 24. One or both of the lips 40 may include a number of bosses 41 extending therefrom. These bosses 41 keep the opposing lips 40 spaced apart in a closed state of the container so that the ETO (ethylene oxide) sterilization gas can readily permeate into the container.

The container 24 is desirably configured to be reclosable. In this manner, the container 24 provides a convenient device for storing used articles prior to disposal. The container 24 may be variously configured so that it is reclosable by, for example, providing a pair of bosses 44 disposed on the lid 34 that mate to a pair of detents 46 that are disposed on the base 36. Other mechanisms that may be useful to reclose the container 24 include but are not limited to adhesives, hook-and-loop fasteners, locking arms, and the like.

Embossing, such as embossing 52 in FIG. 3, may be disposed on the outer surface 48 of the lid 34 or on the outer surface 50 of the base 36. Alphanumeric, numeric or other characters may be embossed on the container 24.

The tray 22 and container 24 are illustrated as generally rectangular in the figures. However, it should be appreciated that these components may take on any convenient shape.

Referring to FIG. 3, the container 24 may be adapted to hold a variety of accessory medical articles including, for example, suture strands (packaged) 112A, swabs (i.e., povidone-iodine prep swabsticks) 124A, lidocaine insert 122A, fenestrated gauze pads 108A, gauze pads 108B, fenestrated drape 129A, single-use packages of lubricant 130A, single-use packages of ointment 124B (i.e., povidone-iodine ointment), antibiotic ointment 128A, sponges, and the like. As described, the container is particularly well suited for retaining these devices after they have been used for later disposal.

As shown in the Figures in general, the tray 22 may include a first planar surface 64. Several recesses are disposed in surface 64, including two recesses 76 that may be used to hold or support coiled articles and a needle recess 81. The recesses 76 can be seen particularly in FIGS. 5 and 6 and may be, for example, generally circumferentially extending recesses that extend around at least a portion of a generally circular structure that defines planar surface 68, as described in greater detail below. The needle recess 81 may include two elongated recesses 80 and 82 so that the needle recess 81 may hold two needles securely. In selected embodiments, recess 80 may be configured to hold a filter needle 80A and the recess 82 may be configured to hold a needle 82A. A recess 90 may be disposed in the first surface 64 and may be configured to hold a looped placement wire 90A for "pull" type PEG procedures. In some embodiments, the looped placement wire 90A may be coiled around a spool and the recess 90 may be rounded to easily accept and hold the looped placement wire 90A.

The first surface 64 may also include a recess 103 that may be configured to have elongated portions 104 and 105. A pair of surgical scissors 104A may be disposed in the portion 104 of the recess 103, and a hemostat 105A may be disposed in the portion 105 of the recess 103.

Figure 2:
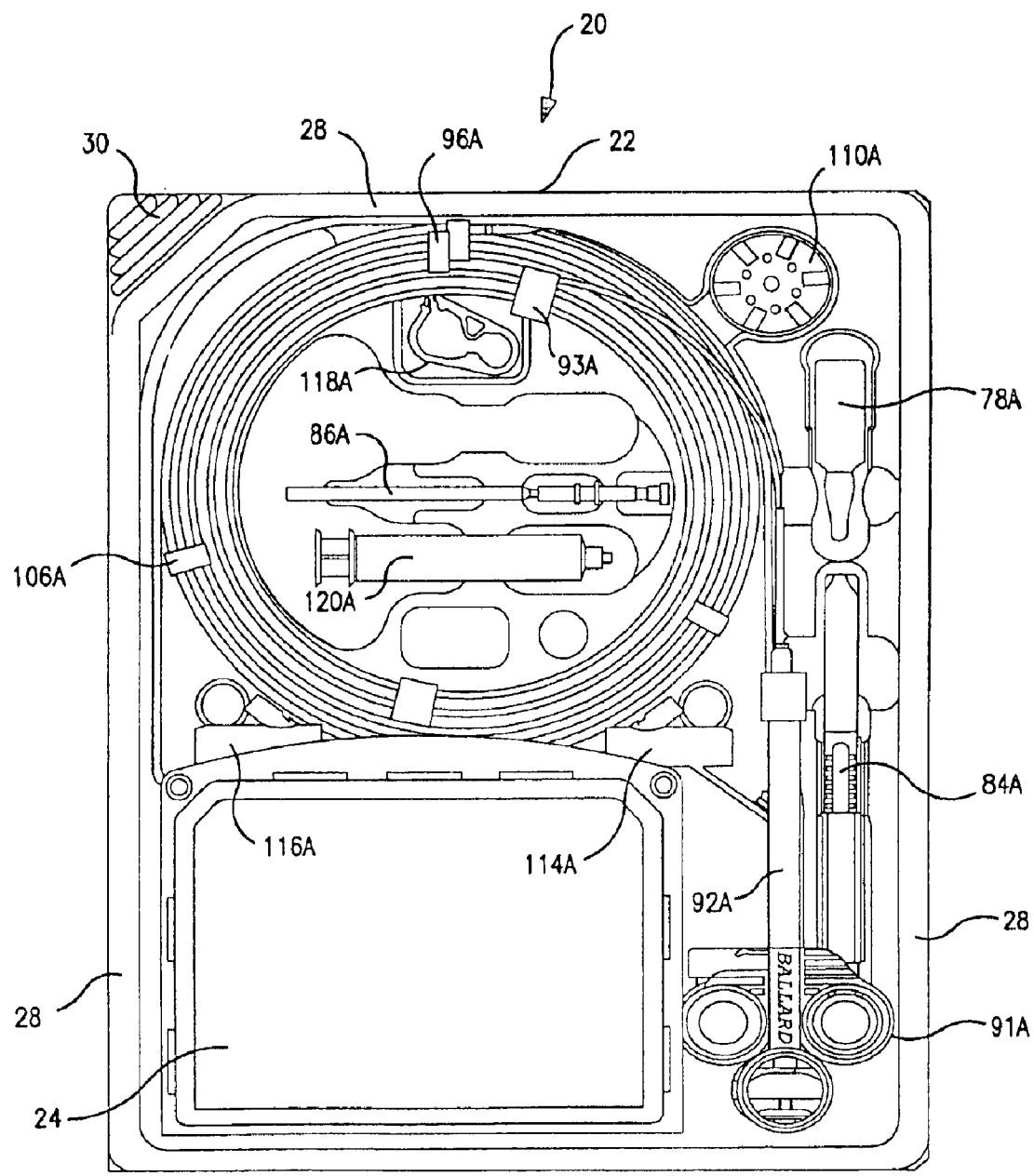
FIG. 2 is a top plan view of the embodiment shown in FIG. 1 with the articles placed in their respective recesses.

The first surface 64 may also include a recess 115 that may be elongated and have two spaced apart ends 114 and 116. As shown in FIGS. 1 and 2, a bolus feeding adapter 114A may be at least partially disposed in the end 114 of the recess 115. A universal feeding adapter 116A may also be at least partially disposed in the end 116 of the recess 115.

The first planar surface in the illustrated embodiment also defines a nesting place for the container 24. An elongated boss 126 may be disposed on the first planar surface 64 for this purpose. This boss 126 and two of the tray side walls 23 cooperate to define a recess or storage location for the container 24 on the first planar surface 64. The container 24 actually rests on the surface 64 above a number of the article recesses. For example, referring to FIGS. 1, 5, and 6 the recesses 80, 81, 82, 90, 103, 104, and 105, as well as their associated articles, are all disposed under the container 24. The physician must first remove the container 24 to gain access to these recesses.

Figure 4:
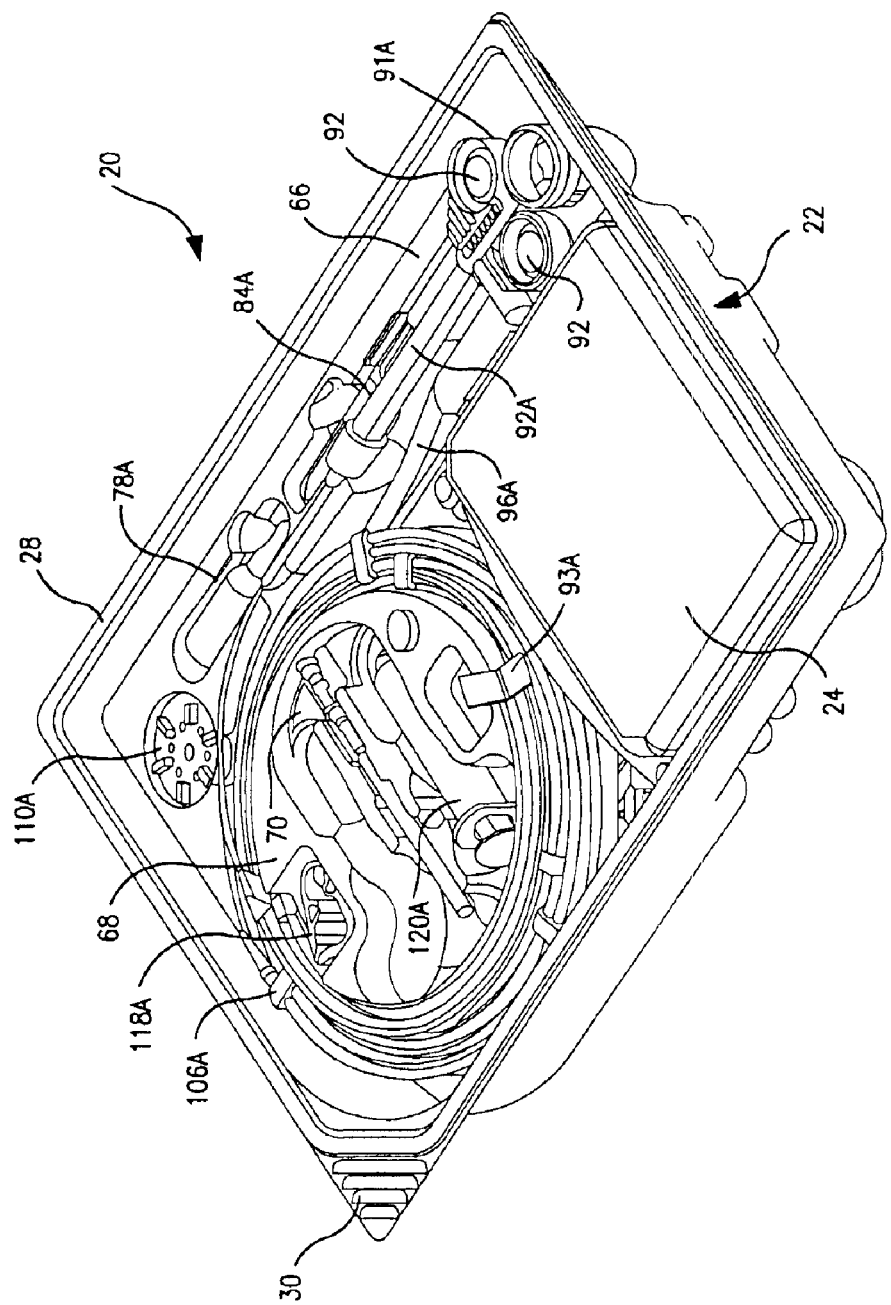
FIG. 4 is a perspective view of an embodiment of a tray and stored articles, including the container.
Figure 5:
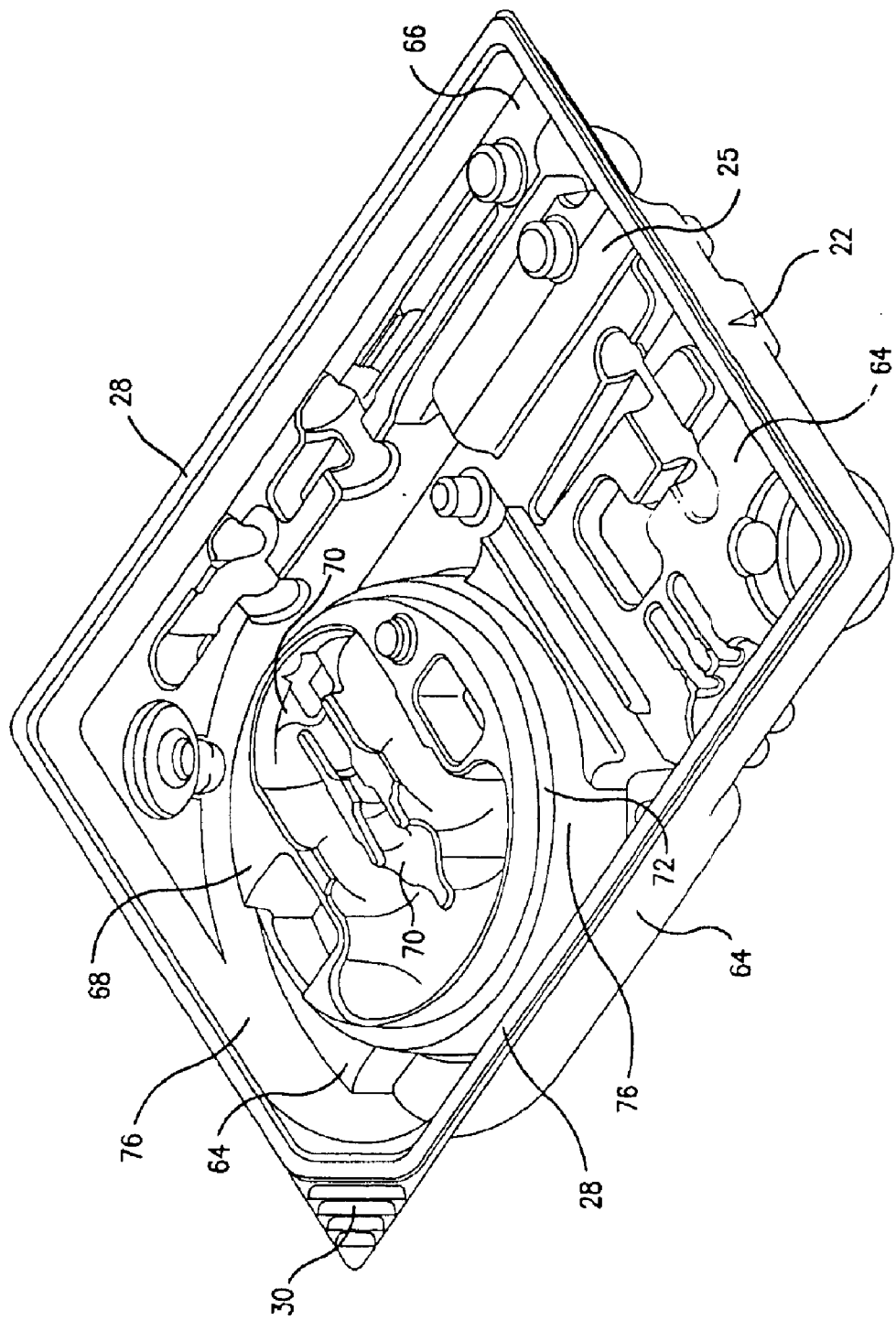
FIG. 5 is a perspective view of the tray according to FIG. 4 without the articles contained therein.
Figure 6:
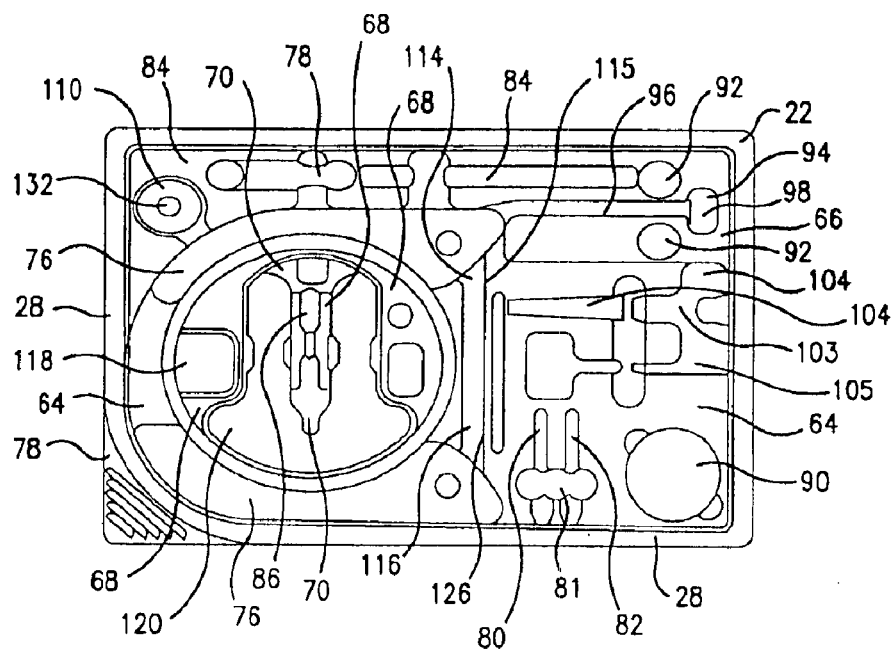
FIG. 6 is a top plan view of the tray according to FIG. 5.
Figure 7:
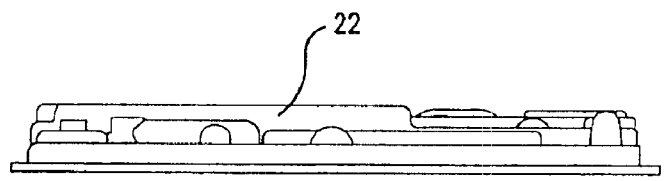
FIG. 7 is a side view of the tray according to FIG. 5.
Figure 8:
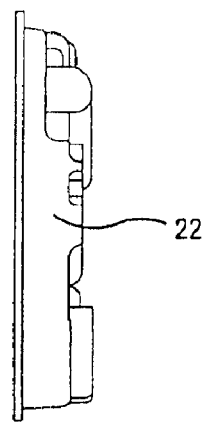
FIG. 8 is an end view of the tray according to FIG. 5.

As seen in FIGS. 4–6, a second planar surface 66 may also be provided and may, in selected embodiments, be offset from the first planar surface 64. Numerous recesses may be disposed in the second planar surface 66 including a recess 78 that is adapted to hold a container of lidocaine 78A and a recess 84 that may be adapted to hold a scalpel 84A, as shown in FIG. 4.

A recess 110 may also be provided in the second planar surface 66, the recess 110 being adapted to hold an exterior tube retention device 110A. In some embodiments, a SECUR-LOK™ ring, available from Ballard Medical Products in Draper, Utah, may be used as an exterior tube retention device 110A. A boss 132 may be disposed in the recess 110 to support the exterior tube retention device 110A.

The second planar surface 66 may also include a recess 94 that is adapted to hold at least a portion of a percutaneous endoscopic gastrostomy (PEG) tube 94A, as seen in FIG. 1. Such a PEG tube typically includes an internal retention device such as a bumper 98A and an elongated tube 96A. For a "pull" type PEG procedure, a loop is provided at the end of the tube 96A. For a "push" type of PEG procedure, an elongated tapered tip 100A is provided at the end of the tube 96A. The recess 94 may include a rounded portion 98 that will hold the bumper 98A. The recess 94 may also include an elongated portion 96 that will hold at least a portion of the elongated tube 96A. The portion of the elongated tube 96A that is not disposed in the elongated portion 96 of the recess 94 may be coiled and placed within the recesses 76 that are formed in the first planar surface 64. In such an embodiment, a portion of the coiled elongated tube 96A may rest on the portions of the first planar surface 64 that are disposed between the recesses 76.

One or more bosses 92 may be disposed on the second planar surface proximate to the recess 94, one boss 92 being disposed on one side of the recess 94 and another boss 92 being disposed on the other side of the recess 94. In such an embodiment, a retrieval snare 92A, as seen in FIG. 4, may be positioned on the second planar surface so that the handle 91A of the retrieval snare 92A is secured in place by the bosses 92. In such an embodiment, at least a portion of the retrieval snare 92A is positioned over the PEG tube 94A, the bumper 98A being disposed under the handle 91A of the retrieval snare 92A. The coiled end 93A of the retrieval snare 92A may be disposed over a portion of the coiled tube 96A of the PEG tube 94A so that both coils 93A and 96A are supported by the first planar surface 64 and may be at least partially disposed in the recesses 76.

For "push" type PEG procedures, a coiled sheathed guide wire 106A may be provided in the kit, as seen in FIGS. 1, 2, and 6. The guide wire 106A may be placed in the recess 76 on top of the coiled end of the snare 93A and coiled tube 96A of the PEG tube 94A.

A third planar surface 68 may also be provided in the tray 22. The third planar surface may be offset from the first planar surface 64, from the second planar surface 66, or from both the first and second planar surfaces 64 and 66, respectively. In the embodiment depicted in the Figures, the third planar surface 68 may be disposed within the interior of the coils 93A and 96A. A recess 120 may be formed in the third planar surface as shown in FIG. 9. The recess 120 may be configured to hold one or two twelve-ounce syringes 120A. A recess 118 may also be disposed in the third planar surface 68 and may be adapted to hold a tubing clamp 118A. The planar surfaces 64, 66, and 68 may all be at least partially outside of the perimeter defined by one another in accordance with one or more exemplary embodiments of the present invention.

A fourth planar surface 70 may be disposed adjacent to the third planar surface 68, as seen in FIGS. 4 and 5. A recess 86 that is adapted to hold an introducer cannula 86A may be formed in the third and fourth planar surfaces 68 and 70, respectively.

In selected embodiments and as shown in FIG. 5, a fifth planar surface 72 may be provided that is adjacent to the fourth planar surface 70. The fifth planar surface 72 may be configured to provide additional support to the coils 93A and 96A.

The tray 22 may also be configured to hold a pamphlet (not shown) that may contain various information such as, for example, directions for using the PEG kit 20.

From the foregoing description, it should be appreciated that the arrangement of the vertically offset planar surfaces and their respective article recesses results in an arrangement wherein certain of the articles must be removed from the kit before unobstructed access is provided to certain underlying articles. The articles are arranged so that, desirably, such articles can be readily removed from the tray in their order of use. For example, in the embodiment illustrated in the Figures wherein the surgical kit is a PEG kit, the container 24 contains many of accessory items needed to prep the surgical site on the patient. The container is seated in its recess on the first planar surface 64 and is readily removable upon removing the cover 26 from the tray 22. The snare device 92A within recess 92 is used before the PEG tube 94A within recess 94, and the snare device 92A must be removed before the PEG tube 94A can be removed. The feeding adapters 114A and 116A within respective recesses 114 and 116 are used towards the end of a PEG procedure and access to the adapters is provided after removal of the snare 92A and PEG tube 94A.

The invention may be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A surgical kit, comprising:
   an integral tray;
   a plurality of surgical articles comprising a first, second and third surgical article;
   a first planar surface defined within the tray and defining a first planar surface recess disposed therein, said first surgical article being disposed in the first planar surface recess;
   a second planar surface defined within the tray and defining a second planar surface recess disposed therein, said second surgical article being disposed in the second planar surface recess, the second planar surface being vertically offset from the first planar surface; and
   a third planar surface defined within the tray and defining a third planar surface recess disposed therein, said third surgical article being disposed in the third elanar surface recess, the third planar surface being vertically offset from the first planar surface and the second planar surface; and
   wherein said first, second, and third planar surfaces are all at least partially outside of the perimeter defined by one another, and wherein said first and second planar surface recesses are positioned within said tray and said first and second surgical articles are disposed in said tray such that the second surgical article must be removed from said tray prior to access being provided to the first surgical article, said first, second and third surgical articles correspondingly arranged in said tray such that unobstructed access is provided to said first, second and third surgical articles in their order of use for a particular surgical procedure.

2. A surgical kit, comprising:
   an integral tray;
   a first planar surface defined within the tray and defining a first planar surface recess disposed therein, a first surgical article disposed in the first planar surface recess;
   a second planar surface defined within the tray and defining a second planar surface recess disposed therein, a second surgical article disposed in the second planar surface recess, the second planar surface being vertically offset from the first planar surface; and
   a third planar surface defined within the tray and defining a third planar surface recess disposed therein, a third surgical article disposed in the third planar surface recess, the third planar surface being vertically offset from the first planar surface and the second planar surface; and
   wherein the second planar surface is at least partially outside of the perimeter defined by the first planar surface, and wherein said first and second planar surface recesses are positioned within said tray and said first and second surgical articles are disposed in said tray such that the second surgical article must be removed from said tray prior to access being provided to the first surgical article, said first and second articles correspondingly arranged in said tray such that unobstructed access is provided to said first and second articles in their order of use for a particular surgical procedure; and
   a removable container adapted to fit at least partially within said tray, said container adapted to rest upon at least a portion of said first planar surface while providing access to at least one said recess defined in said first planar surface, said container being reclosable and containing at least one accessory article useful in performing the surgical procedure.

3. The surgical kit as in claim 2, further comprising a plurality of said recesses defined in said first planar surface below said container such that said container must be removed from said tray prior to having access to articles contained in said recesses below said tray.

4. The surgical kit as in claim 1, further comprising a cover adapted to be placed over said tray.

5. The surgical kit as in claim 1, further comprising at least one boss extending upwardly from at least one of said planar surfaces, said boss configured for extending through at least a portion of a surgical article.

6. The surgical kit as in claim 5, wherein said boss extends through a handle portion of a snare device.

7. A surgical kit, comprising:
   a tray comprising a plurality of planar surfaces defined therein;
   a plurality of article recesses defined in said planar surfaces such that at least one said recess is defined in each of said planar surfaces, each said recess having a shape for receipt of a particular surgical article therein; and
   wherein said planar surfaces are arranged such that each said planar surface is offset vertically with respect to at least one other said planar surface and said recesses positioned within said tray such that articles in at least one upper said planar surface must be removed from said tray prior to access being provided to articles in at least one lower said planar surface, said articles correspondingly arranged in said tray such that unobstructed access is provided to said articles in their order of use for a particular surgical procedure;
   further comprising at least one boss extending upwardly from at least one of said planar surfaces, said boss configured for extending through at least a portion of a surgical article;
   wherein said boss extends through a handle portion of a snare device; and wherein said snare device overlies at least a portion of another said article received in a recess defined below the position of said snare device.

8. The surgical kit as in claim 7, wherein said article in said recess below said snare device comprises a percutaneous gastrostomy tube.

9. The surgical kit as in claim 8, further comprising a coiled guide wire overlying a portion of said percutaneous gastrostomy tube.

10. A percutaneous endoscopic gastrostomy (PEG) kit comprising:
   a tray, said tray further comprising
      a first planar surface comprising at least one recess disposed within the first planar surface,
      a second planar surface comprising at least one recess disposed within the second planar surface, the second planar surface being offset from the first planar surface,
      a third planar surface comprising at least one recess disposed within the third planar surface, the third planar surface being offset from the first planar surfaces
      a container at least partially fitting within the tray, the container resting upon at least one of the plurality of planar surfaces while leaving at least one said recess in said planar surface exposed, wherein the planar surface onto which the container rests is at least partially outside of the perimeter defined by at least two of the other planar surfaces of the tray, the container adapted to be reclosable and to retain accessory articles useful in performing a medical procedure; and
   a cover adapted to be placed over the tray;
   wherein each recess is adapted to hold at least one article useful in performing a medical procedure.

11. The PEG kit as in claim 10, wherein at least one said recess disposed in said first planar surface is adapted hold a looped placement wire.

12. The PEG kit as in claim 10, wherein at least one said recess disposed in said second planar surface is adapted to hold at least a portion of a percutaneous endoscopic gastrostomy tube.

13. The PEG kit as in claim 12, wherein said percutaneous endoscopic gastrostomy tube comprises a bumper, said bumper disposed within at least one said recess in said second planar surface.

14. The PEG kit as in claim 10, wherein at least one said recess disposed in said third planar surface is adapted to hold an introducer cannula.

15. The PEG kit as in claim 10, wherein said cover rests on a peripheral edge of said tray.

16. The PEG kit as in claim 10, wherein at least one said recess disposed in said first planar surface is adapted to retain at least a portion of a guide wire.

17. The PEG kit as in claim 10, wherein at least one said recess disposed in said second planar surface is adapted to retain an exterior tube retention device.

18. The PEG kit as in claim 10, wherein said container rests on at least a portion of said first planar surface.

19. A percutaneous endoscopic gastrostomy (PEG) kit comprising:
   a tray, said tray further comprising
      a first planar surface comprising at least one recess disposed within the first planar surface,
      a second planar surface comprising at least one recess disposed within the second planar surface, the second planar surface being offset from the first planar surface,
      a third planar surface comprising at least one recess disposed within the third planar surface, the third planar surface being offset from the first planar surface
      a container at least partially within the tray, the container resting upon the first planar surface while leaving at least one said recess in said first planar surface exposed, the container adapted to be reclosable and to retain accessory articles useful in performing a medical procedure; and
   a cover adapted to be placed over the tray;
   wherein each recess is adapted to hold at least one article useful in performing a medical procedure;
   wherein at least one of said planar surfaces comprises at least one boss extending upwardly from the surface.

20. The PEG kit as in claim 19, wherein said boss extends upwardly from said second planar surface.

* * * * *